(12) United States Patent
Okamura et al.

(10) Patent No.: US 7,332,718 B2
(45) Date of Patent: Feb. 19, 2008

(54) METHOD FOR FINDING DISCONNECTION OF CONDUCTIVE WIRES FORMED ON PLATE GLASS AND APPARATUS THEREFOR

(75) Inventors: Shinichi Okamura, Mie (JP); Masahiko Ookita, Mie (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 10/623,604

(22) Filed: Jul. 22, 2003

(65) Prior Publication Data
US 2004/0124358 A1    Jul. 1, 2004

(51) Int. Cl.
*G01J 5/02* (2006.01)
(52) U.S. Cl. .................................. 250/341.1
(58) Field of Classification Search ............ 250/341.1, 250/330, 332; 702/84; 374/5, 124, 121; 324/501; 438/17
See application file for complete search history.

(56) References Cited

U.S. PATENT DOCUMENTS

| | | | | |
|---|---|---|---|---|
| 5,032,727 A | * | 7/1991 | Cox et al. ................. | 250/330 |
| 5,208,528 A | * | 5/1993 | Quintard ................. | 324/158.1 |
| 5,294,198 A | * | 3/1994 | Schlagheck ............. | 374/4 |
| 5,309,108 A | | 5/1994 | Maeda et al. | |
| 6,024,904 A | * | 2/2000 | Nanri ..................... | 264/104 |
| 6,614,922 B1 | * | 9/2003 | Walton ................... | 382/141 |
| 6,840,666 B2 | * | 1/2005 | Enachescu et al. ...... | 374/5 |
| 6,847,907 B1 | * | 1/2005 | Novotny ................. | 702/84 |

FOREIGN PATENT DOCUMENTS

| | | |
|---|---|---|
| EP | 0535881 A1 | 4/1993 |
| JP | 59-218967 | 12/1984 |
| JP | 2-12046 | 1/1990 |
| JP | 4-72552 | 3/1992 |
| JP | 5-296825 | 11/1993 |
| JP | 5-312882 | 11/1993 |
| JP | 5-340905 | 12/1993 |
| JP | A-6-249905 | 9/1994 |
| JP | 7-151810 A | 6/1995 |
| JP | 10-185527 A | 7/1998 |
| JP | 11-94918 | 4/1999 |
| JP | 2001-180445 A | 7/2001 |
| WO | WO-0107901 A1 | 2/2001 |

OTHER PUBLICATIONS

Office Action in Japanese Patent Application No. 2002-015206 dated Jan. 24, 2006.

* cited by examiner

*Primary Examiner*—David Porta
*Assistant Examiner*—Marcus H Taningco
(74) *Attorney, Agent, or Firm*—Crowell & Moring LLP

(57) ABSTRACT

The invention relates to a method for finding disconnection of a conductive wire formed on a plate glass. This method includes the steps of (a) applying a voltage to the conductive wire; and (b) imaging thermal radiation from a surface of the conductive wire by an infrared image sensor, while the step (a) is conducted, thereby producing a temperature distribution image. An apparatus for conducting the method includes (a) a power source for applying a voltage to the conductive wire; and (b) an infrared image sensor for imaging thermal radiation from a surface of the conductive wire, thereby producing a temperature distribution image.

6 Claims, 3 Drawing Sheets

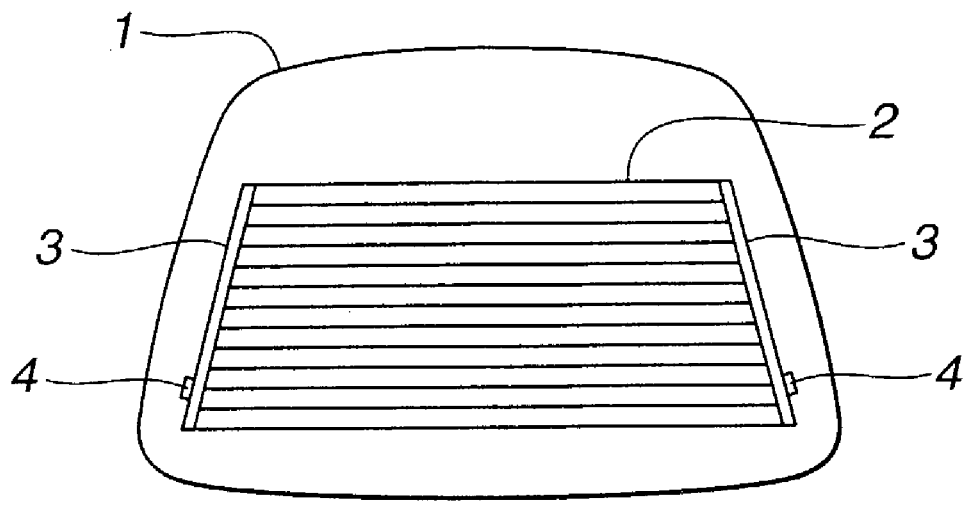
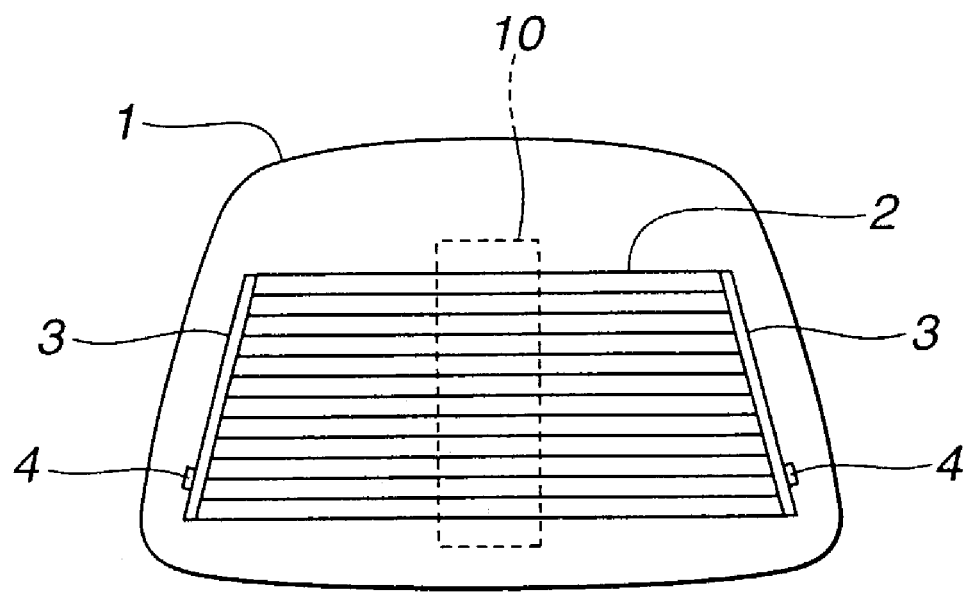

METHOD FOR FINDING DISCONNECTION OF CONDUCTIVE WIRES FORMED ON PLATE GLASS AND APPARATUS THEREFOR

BACKGROUND OF THE INVENTION

The present invention relates to a method for finding the existence or nonexistence of disconnection (breaking) of conductive wires in antifogging glass or antenna glass used in vehicular windows and the like.

A conductive paste is printed on a plate glass by screen printing or the like to form conductive wires thereon. In vehicular plate glass, such conductive wires are used for heating plate glass by applying electricity to the conductive wires to provide antifogging property and are used as an antenna for telecommunication. These functions of conductive wires may be impaired by disconnection of the conductive wires. Therefore, it is necessary before shipping to inspect conductive wires to see if they have disconnection or not.

Japanese Patent Application Publication No. 6-249905 discloses a method for finding disconnection of conductive wires in an antifogging glass. In this method, electromagnetic energy generated by applying a voltage to the conductive wires is detected by a detecting head. Furthermore, a conductive wire position detecting sensor is provided for outputting a detection signal when the detecting head is above the conductive wires. The detecting head, together with the sensor, is moved along the surface of the antifogging glass. The output signals from the detecting head and the sensor are input into a computer to judge whether or not there is disconnection.

Hitherto, finding disconnection of conductive wires has been conducted by moving a sensor along the surface of antifogging glasses in the mass production of antifogging glasses, as disclosed in Japanese Patent Application Publication No. 6-249905. However, the productivity is not so good, since it is necessary to change the manner of moving the sensor for a different type of antifogging glass. Furthermore, it may be difficult to distinguish a first conductive wire having disconnection from a second conductive wire having no disconnection, if the first and second conductive wires are close to each other. Still furthermore, the movement and the position of the sensor may be limited in the case of an antifogging glass having a small curvature (steep curve). With this, the accuracy for finding disconnection may be lowered.

SUMMARY OF THE INVENTION

It is therefore an object of the present invention to provide a method for efficiently finding disconnection of conductive wires formed on a plate glass.

According to the present invention, there is provided a method for finding disconnection of a conductive wire formed on a plate glass. This method includes the steps of:

(a) applying a voltage to the conductive wire; and (b) imaging thermal radiation from a surface of the conductive wire by an infrared image sensor, while the step (a) is conducted, thereby producing a temperature distribution image.

According to the present invention, there is provided an apparatus for finding disconnection of a conductive wire formed on a plate glass, the apparatus comprising:

a power source for applying a voltage to the conductive wire; and an infrared image sensor for imaging thermal radiation from a surface of the conductive wire,. thereby producing a temperature distribution image.

BRIEF DESCRIPTION OF THE DRAWINGS

FIG. 2 is a plan view showing the antifogging glass;

FIG. 3 is a view similar to FIG. 2, but showing an area for conducting a binarization with a dotted line.

DESCRIPTION OF THE PREFERRED EMBODIMENTS

A method of the present invention for finding the existence or nonexistence of disconnection of a conductive wire(s) formed on a plate glass is described in detail, as follows.

Conductive wires can be formed on a plate glass to have a certain predetermined pattern by applying a conductive paste to the plate glass through screen printing or the like. The resulting conductive wires can serve as heating wires of an antifogging glass for providing antifogging property or as antenna wires of an antenna glass.

Figure 1:
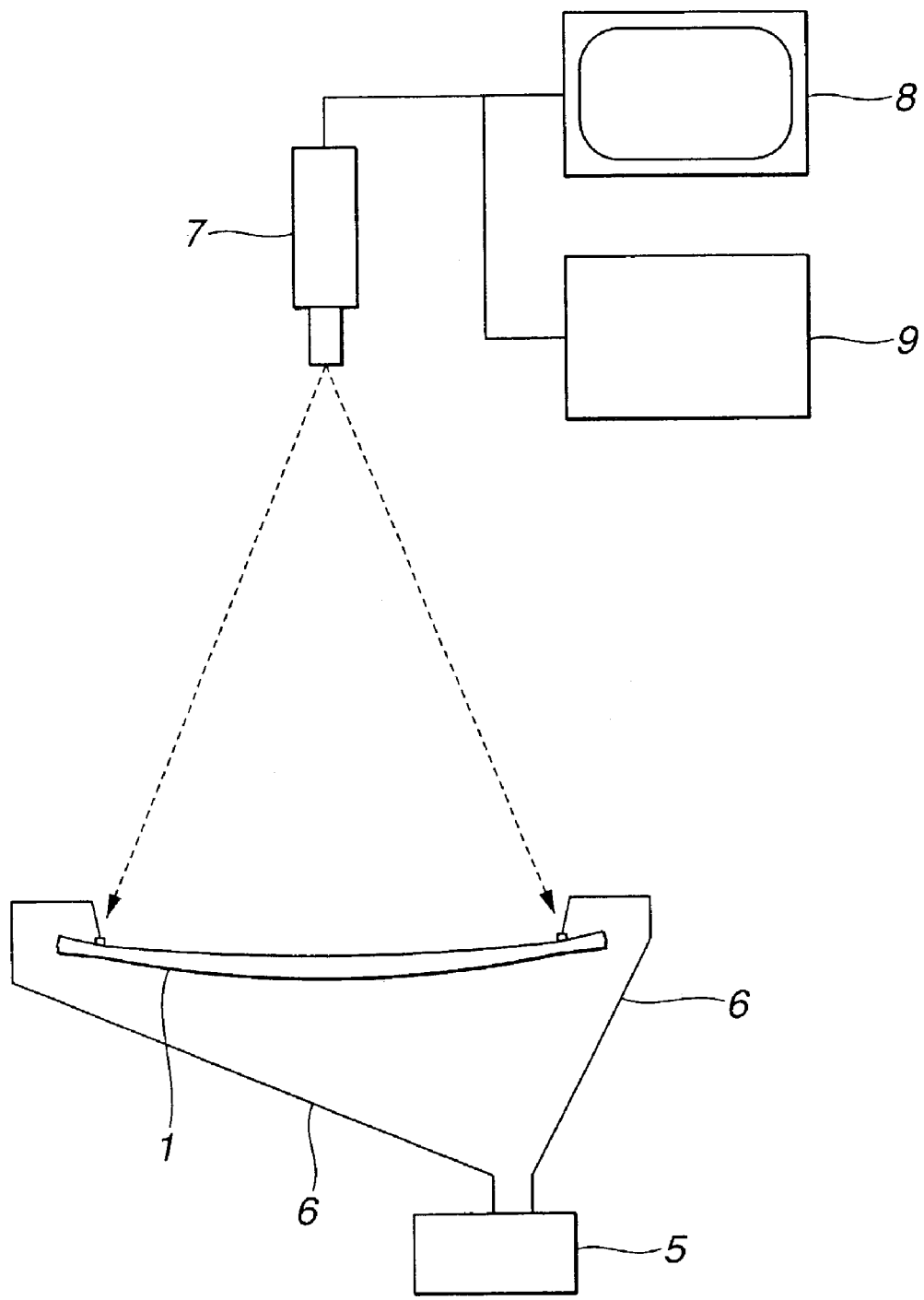
FIG. 1 is a schematic view showing an apparatus for finding disconnection of conductive wires formed on an antifogging glass.

FIG. 1 shows an exemplary apparatus according to the present invention, which is capable of finding the existence or nonexistence of disconnection of conductive wires 2 formed on an antifogging glass 1 of FIG. 2.

The apparatus has a power source for applying a voltage to the conductive wires 2. As is seen from FIG. 1, the power source may be a voltage stabilizer or constant voltage device 5 (preferably of direct current) for controlling the amount of heat generation from the conductive wires or the temperature of the conductive wires upon applying a voltage to the conductive wires.

In case that a conductive wire has no disconnection, heat is generated from the conductive wire by applying a voltage thereto. In contrast, in case that a conductive wire has disconnection, no heat is generated. Thus, it is possible by the present invention to find the existence or nonexistence of disconnection of a conductive wire(s) by imaging thermal radiation from the surface of the conductive wire(s) by an infrared image sensor to produce a temperature distribution image. In other words, if no heat generation has been found at a position in the temperature distribution image, which corresponds to the position of a conductive wire, this conductive wire can be judged as having disconnection. In contrast, if a certain predetermined heat generation has been found at such position, the conductive wire can be judged as having no disconnection. This judgement can easily be conducted by comparing the temperature distribution image of a plate glass with an image data showing the pattern of conductive wires of the plate glass, as described hereinafter.

As is seen from FIG. 2, conductive wires (heating wires) 2 of an antifogging glass 1 are connected to bus bars 3. Therefore, it is possible to apply a voltage to the conductive wires 2 by using feeding terminals 4 of the bus bars 3 or by bringing feeding probes into contact with the bus bars 3.

Figure 4:
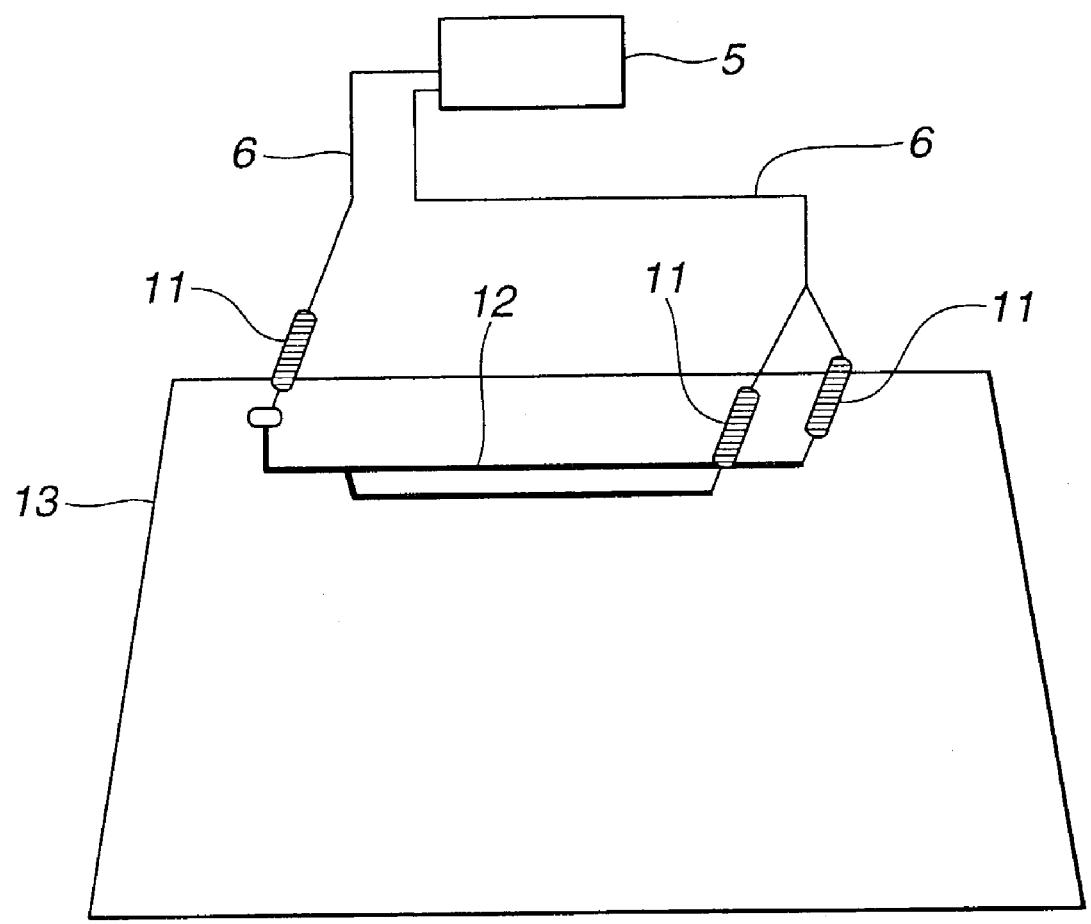
FIG. 4 is a schematic view showing a condition in which a voltage is applied to a conductive wire as antenna.

As is seen from FIG. 4, in case that the conductive wire is an antenna wire 12 formed on a plate glass (antenna glass) 13, the feeding terminal is often provided only at an end or another position of the antenna wire 12. In this case, it is possible to apply a voltage to the antenna wire 12 by using at least two probes 11 (three probes in FIG. 4).

The voltage to be applied to the conductive wire 2 may be adjusted to a value that is appropriate for resistance of the conductive wire 2. If the conductive wire 2 is a heating wire for antifogging glass, the voltage may be from 10V to 50V.

The infrared image sensor of the present invention may be an infrared camera or thermo-tracer. The infrared image sensor may contain an infrared detecting device and an optical system for image formation.

The above-mentioned judgement with respect to disconnection can be made by checking only the temperature distribution image taken by an infrared image sensor. However, as the number of conductive wires increases in an area of a certain size to have a complicated pattern, it may be difficult to judge whether a first case, in which heat generation is not shown at a particular position of the temperature distribution image due to disconnection of a conductive wire, or a second case, in which heat generation is not shown due to nonexistence of a conductive wire, is true. Thus, it is possible to easily conduct the judgement by comparing the temperature distribution image with an image data showing the pattern (distribution) of conductive wires. This image data may be a first image data obtained by drafting the pattern of the conductive wires, for example, by computer-aided design (CAD). The first image data (digital data) obtained by CAD is suitable, since it can be processed in an image processor. The image data may be a second image data obtained, prior to the voltage application, by imaging thermal radiation from the surface of the conductive wire by an infrared image sensor or digital camera.

An image itself (taken by an infrared image sensor or digital camera prior to the voltage application) may be compared with the temperature distribution image (taken by an infrared image sensor under the voltage application) for judging whether or not a conductive wire has disconnection. However, it is preferable to subject both of these images to a binarization by an image processor in order to distinguish the image of the conductive wires from the image of other parts of a plate glass.

The above binarization may be conducted for a part or the entirety of the image in accordance with the range necessary for the disconnection inspection. For example, in case that all of the heating wires 2 are parallel with each other, it suffices that only the image of a rectangular portion 10 (covering all the heating wires 2 as shown in FIG. 3) is subjected to the binarization.

It is possible to easily compare the temperature distribution image (taken under the voltage application) with a data representing the pattern of the conductive wires by superimposing the temperature distribution image on this data to have these on the same screen. Furthermore, it is possible to conduct a subtraction by an image processor between the temperature distribution image and the data, thereby clearly showing only conductive wires having disconnection on the screen. In this way, it is possible by the present invention to automatically find the existence or nonexistence of disconnection of conductive wires.

In case that a data representing the pattern of the conductive wires is an image (digital) data obtained by CAD, an infrared image sensor or digital camera, such image data can be used in the above-mentioned superimposition and subtraction. Even in case that a data representing the pattern of the conductive wires is a data (analogue data) obtained by drafting the pattern on paper or the like, it is preferable to convert such analogue data to an image data (digital data) by using a digital camera or the like.

The following nonlimitative Example is illustrative of the present invention.

EXAMPLE 1

Prior to the voltage application, the image of the pattern of heating wires 2 of an antifogging glass 1 (shown in FIG. 2) was taken by an infrared image sensor (i.e., an infrared camera of Nippon Avionics Co., Ltd.) 7 of FIG. 1.

Then, a voltage of 20V was applied by connecting a voltage stabilizer (constant voltage device) 5 to feeding terminals 4 of an antifogging glass 1 through feeding wires 6. Under this condition, the image of the pattern of the heating wires 2 was taken by the infrared camera 7. This image taken by the infrared camera 7 was shown in a monitor 8 and compared with the image prior to the voltage application to find the existence or nonexistence of disconnection of the heating wires.

EXAMPLE 2

The two images (prior to and under the voltage application) obtained in Example 1 were subjected to a binarization by an image processor 9 made by Yokogawa MAT Corporation, thereby obtaining two image data showing only the heating wires. These two image data were subjected a subtraction, and the result was shown in the monitor 8. In fact, each image remaining after the subtraction was judged as representing one heating wire having disconnection. This judgement was conducted automatically.

EXAMPLE 3

The same steps as those of Examples 1 and 2 were conducted sequentially, except in that the infrared camera of Example 1 was replaced with a thermo-tracer made by NEC san-ei Instruments Co. With this, it was possible to find the existence or nonexistence of disconnection of the conductive wires (heating wires) 2.

The entire contents of Japanese Patent Application No. 2002-015206 (filed Jan. 24, 2002), which is a basic Japanese application of the present application, are incorporated herein by reference.

What is claimed is:

1. A method for finding disconnection of a plurality of conductive wires that are formed on a vehicular plate glass and are parallel with each other, the method comprising the steps of:

(a) applying a voltage to the conductive wires;

(b) imaging thermal radiation from a surface of the conductive wires by an infrared image sensor, while the step (a) is conducted, thereby producing a temperature distribution image;

(c) selecting an inspection portion from the temperature distribution image, the inspection portion having a size to cover only a portion of each conductive wire;

(d) subjecting only the inspection portion of the temperature distribution image having a size less than the entirety of each conductive wire to a binarization by an image processor, thereby producing a binarized temperature distribution image of only the inspection portion; and (e) comparing the binarized temperature distribution image with a data representing a pattern of the conductive wires to determine whether a disconnection exists anywhere in the entirety of the conductive wires, based on the binarized temperature distribution image of only the inspection portion.

2. A method according to claim 1, wherein the data of the step (e) is a first image data obtained by drafting the pattern of the conductive wire.

3. A method according to claim 1, wherein the data of the step (e) is a second image data obtained, prior to the step (a), by imaging thermal radiation from the surface of the conductive wires by the infrared image sensor.

4. A method according to claim 1, wherein the comparison of the step (e) is conducted by superimposing the binarized temperature distribution image on the data.

5. A method according to claim 1, wherein the comparison of the step (e) is conducted by an image data subtraction between the binarized temperature distribution image and the data.

6. A method according to claim 1, wherein the conductive wires serve as heating wires for providing an antifogging property or as antenna wires.

* * * * *